(12) United States Patent
Paolicchi et al.

(10) Patent No.: US 8,486,650 B2
(45) Date of Patent: Jul. 16, 2013

(54) METHOD OF DETECTING SERUM GAMMA-GLUTAMYL TRANSFERASE ISOFORMS IN A BIOLOGICAL FLUID

(75) Inventors: Aldo Paolicchi, San Giuliano Terme (IT); Alfonso Pompella, Pisa (IT); Maria Franzini, Calci (IT); Renata Barsacchi, Localita S. Maria del Giudice (IT); Michele Emdin, Pisa (IT); Emilia Bramanti, Pietrasanta (IT)

(73) Assignee: Universita' di Pisa, Pisa (IT)

( * ) Notice: Subject to any disclaimer, the term of this patent is extended or adjusted under 35 U.S.C. 154(b) by 420 days.

(21) Appl. No.: 12/665,952

(22) PCT Filed: Jun. 24, 2008

(86) PCT No.: PCT/IB2008/052499
§ 371 (c)(1), (2), (4) Date: Dec. 22, 2009

(87) PCT Pub. No.: WO2009/001290
PCT Pub. Date: Dec. 31, 2008

(65) Prior Publication Data
US 2010/0227351 A1     Sep. 9, 2010

(30) Foreign Application Priority Data
Jun. 25, 2007   (IT) .............................. TO2007A0455

(51) Int. Cl.
*C12Q 1/48*   (2006.01)
(52) U.S. Cl.
USPC .......................................................... 435/15
(58) Field of Classification Search
USPC .......................................................... 435/15
See application file for complete search history.

(56) References Cited

U.S. PATENT DOCUMENTS 5,591,589 A * 1/1997 Katoh et al. ................ 435/7.1

FOREIGN PATENT DOCUMENTS

GB   2103607       2/1983
GB   2103607 A  *  2/1983

OTHER PUBLICATIONS

Del Corso A. et al. Colorimetric Coupled Enzyme Assay for Gamma Glutamyltransferase Activity Using Glutathione as Substrate. J Bioochem Biophys Methods 67:123-130, Jun. 30, 2006.*
Senen A. et al. Activity Determination, Kinetic Analyses and Isoenzyme Identification of GGT in Human Neutrophils. J of Biochemistry and Molecular Biology 38(3)343-349, May 2005.*
Echetebu et al "Multiple Forms of Human γ-Glutamyltransferase" Enzyme 27: 1982, pp. 1-8.
Wenham et al "Physical Properties of γ-Glutamyltransferase in Human Serum" Clinica Chimica Acta etc, Aug. 1984, pp. 205 and 215-217.
Wenham et al "γ-Glutamyltransferases in Bile and Sera from Patients with Extrahepatic Biliary Obstruction", Clinica Chimica Acta et c. Apr. 1981, pp. 113-122.
Franzini et al "A High Performance Gel Filtration Chromatography Method for γ-Glutamyltransferase Fraction Analysis", Analytical Biochemistry, Academic Press, Oct. 207, pp. 1-6.
Franzini et al "Fractions of Plasma Gamma-Glutamyltransferase in Healthy Individuals: Reference Values", Clinica Chimica Acta etc., Sep. 2008, pp. 188-189.

* cited by examiner

*Primary Examiner* — Ralph Gitomer
(74) *Attorney, Agent, or Firm* — Ladas & Parry, LLP

(57) ABSTRACT

A method is described for detecting the gamma-glutamyl transferase enzyme isoforms (GGT, EC 2.3.2.2) in a sample of biological fluid, such as for example plasma or serum. The method comprises an HPLC separation step of the sample proteins based on the molecular size and a second step for detecting the GGT isoforms by post-column reaction with a GGT enzyme substrate capable of generating a detectable final product, preferably by spectrophotometric or fluorimetric means. The GGT isoforms can be separated by ultracentrifugation, thereby obtaining three enzymatic isoforms characterized by molecular weights of approximately 2000, 940, and 140 KDa, respectively.

11 Claims, 4 Drawing Sheets

METHOD OF DETECTING SERUM GAMMA-GLUTAMYL TRANSFERASE ISOFORMS IN A BIOLOGICAL FLUID

This application is a National Stage application which claims benefit to PCT/IB08/52499 filed Jun. 24, 2008.

The present invention relates to a method of detecting and separating isoforms of the serum gamma-glutamyl transferase (sGGT) enzyme, which are present in a sample of biological fluid such as for example serum or plasma, as well as the enzymatic isoforms obtained by the method of the invention.

Gamma-glutamyl transferase (EC 2.3.2.2, also referred to as gamma-glutamyl transpeptidase) is an enzyme found in blood (5), in the majority of the biological fluids, and on the plasma membrane of most cell types. Some tissues, such as kidney cortex, brain choroid plexa, bile structures, the lactating mammary gland, are particularly rich in GGT (6). The majority of the solid tumours (7), as well as the T leukaemia cells both myeloid and lymphoid (8), are also particularly rich in GGT.

GGT is the only enzyme capable of catalysing the hydrolysis of glutathione (GSH), the most important anti-oxidant in mammal cells (9). The fact that GGT is localised on the outer surface of the cell membrane suggests that its substrate will mainly be extra-cellular GSH, and experimental results achieved by the present inventors have provided evidence for this. Glutathione hydrolysis, although having a physiologic function in recovering GSH in kidney tubular cells and in the other usually GGT-containing tissues, has noxious consequences in pathological tissues, by producing reactive oxygen species, free radicals and triggering oxidative events upon cell structures (10). Moreover, in tumour cells, the expression of high GGT activities makes them resistant to anti-tumour chemotherapeutic agents, by virtue of the particular reactivity of the GSH extra-cellular hydrolysis products, which are able to interact with and inactivate drugs (11).

The physiological functions of the GGT that is present in the blood circulation, that is to say serum GGT (sGGT), have not been so far well defined, but sGGT activity is known to vary according to age, sex, physiological condition and as a consequence of such pathologies as the hepatobiliar ones and alcoholism. For this reason, sGGT activity assays are commonly used as tests in clinical chemistry, since sGGT levels are regarded as a marker for hepatobiliar pathologies and alcohol consumption.

High (pathological) sGGT values are detected in many patients, but a kidney disease is actually diagnosed or alcohol abuse is confirmed only in a very low percentage of cases. Many patients are subjected to long and expensive diagnostic procedures (such as e.g. laboratory examinations, ultrasound scanning, kidney biopsy, etc.) without this eventually leading to any diagnosis of an existing pathology.

Furthermore, in recent years, irrespective of the presence of a kidney pathology, sGGT resulted as one of the most strong predictors of morbidity and premature mortality. Works published in the last decade have in fact demonstrated that sGGT levels up to now considered non-pathologic, although lying on the high side (sGGT>25 U/L) of the reference range (sGGT 5-50 U/L), associated with increased cardiovascular mortality and the risk of diabetes (1, 2, 3). Even more recently, the sGGT level determined upon recovery has been shown to be the strongest indicator of adverse progression in many pathologies, not only the cardiovascular ones but also the neoplastic, degenerative, and other ones (4). It is clear that such a strong mortality and morbidity indicator could be clinically very useful, although the very broad range of its predictive value does not make it possible to predict, by using the sGGT determination alone, the pathology that will affect the patient, still less its outcome, nor to direct the subsequent diagnostic-therapeutic procedures. For this reason, the determination of serum GGT activity is considered to be a sensitive and accurate laboratory test, but unfortunately not a specific one.

In fact, even if the determinants of the sGGT levels are known, little is known regarding the origin, nature, functions and fate of this enzyme. Among the positive determinants are for example alcohol consumption, drug consumption—including the oral contraceptives—age, diseases such as diabetes, arterial hypertension and hypercholesterolaemia, whereas among the negative determinants are exercise, coffee consumption and pulmonary ventilation capacity (1).

Many investigations have been directed to the study of the different GGT isoenzymes (12), in an attempt to establish a correlation with specific pathologies and/or different source tissues.

In fact, since a single gene able to encode active GGT has been identified in the human being (13), it is not completely correct to use the term "isoenzyme" to refer to the different detectable GGT forms; rather it appears more correct to use the general term isoform.

It has long been known that, by using various methods, it is possible to distinguish the GGTs originating from different tissues, as well as the different forms of serum GTT, as it is possible to demonstrate the appearance of different GGT forms in the course of diseases, or at least the change in the pattern of the different GGT forms.

In order to detect and separate the GGT isoforms, different techniques have been used, which however give rise to two important problems. The first consists of the low sensitivity of the determination, while the second is caused by the extreme protein lypophilicity which in many cases makes it necessary to proteolytically digest the GGT with the aim of achieving the detachment of the terminal lypophilic portion in order to allow for the analysis of the protein in liquid systems.

By using gel filtration, agarose gel electrophoresis, isoelectrofocusing, lectin affinity or anionic exchange chromatography techniques (that is procedures that contemplate the proteolytical digestion of the enzyme and that are usable both on tissue extracts and plasma), it has been possible to prove that different tissues produce the same enzymatic protein but with a different glycosylation and therefore a different surface electrostatic charge (14).

As regards to serum GGT, it appears homogeneous with some techniques (for instance anionic exchange) but heterogeneous with others (for instance agarose gel or cellulose acetate electrophoresis). Thanks to the studies done by Huseby (5, 15) such ostensible incongruity has been clarified: only the kidney-derived GGT is present in the blood circulation, so the enzyme detectable in a biological fluid such as plasma, serum or urine has a homogeneous appearance when using techniques that involve proteolysis and perform separation on the basis of the electrostatic charge, whereas, when using techniques that do not involve proteolysis, the identification of different isoforms depends on, at least in part, the ability of GGT to associate with the different plasma lipoproteins (16).

Unfortunately, the low sensitivity of these techniques has allowed the heterogeneity problem to be studied only in patients with high GGT readings (such as for example subjects affected with cholestasis), thus the mechanisms, determinants and precise physiopathologic correlation of the association of serum GGT with the different lipoproteins have not been clarified yet, nor it is really certain whether the only GGT that is present is the hepatic type even at normal levels of serum enzymatic activity.

Presently, the GGT chemo-clinical determination is preformed with a kinetic-enzymatic assay (17) based on the breakdown of a chromogenic substrate (gamma-glutamyl-4-nitroanilide or gamma-glutamyl-3-carboxy-4-nitroanilide), releasing a coloured product (4-nitroaniline) in a quantity proportional to GGT activity in the sample.

The assaying of the GGT isoforms has been commercially proposed with a device (Beckman Paragon) that basically entails electrophoresis of the serum proteins on a cellulose acetate support (analogous to normal electrophoresis of serum proteins) and detection of the presence of GGT bands co-migrating with the serum proteins, with the aid of a substrate that produces a coloured product that is proportional to the amount of GGT in the band (18). In such a way, a graph is obtained in which different GGT bands are detectable, and in particular a GGT band that co-migrates with albumin is detected, as well as various other bands that co-migrate next to serum lipoproteins. With such a procedure it is not possible to determine if the GGT is physically associated with albumin and lipoproteins or if it just produces bands that migrate with the same speed on the support.

The issue of the nature of the different GGT isoforms has attracted marginal interest in recent years, as it has not been possible to identify any pathologic correlation between the presence/absence or the absolute or relative intensity of the different GGT isoforms and the diseases studied (the only exception being hepatocarcinoma; 19, 20). This failure was primarily caused by the fact that, up to now, GGT has been mistakenly considered merely to be a marker for hepatobiliar damage or alcohol abuse. For these reasons, such a technique has never come into a clinical use.

Recently, due to studies performed by the present inventors, it has been proved that:
1) GGT is a cardiac risk factor (21);
2) GGT is found within the atherosclerotic plaque (accountable for such pathologies as heart attack and stroke) both in cerebral and carotid and cardiac lesions (10, 22,23);
3) within the atherosclerotic plaque GGT is complexed to oxidized lipoprotein deposits (22);
4) GGT itself is capable of causing oxidation of LDL lipoproteins (24), and this event is thought to be crucial both for the formation of the atherosclerotic plaque and the destabilisation thereof, which causes the terminal consequences of atherosclerotic disease, that is heart attack and stroke.

For these reasons, the detailed study of the association of GGT both with the lipoproteins that cause atherosclerosis (for instance LDL and Lipoprotein (a)) and with the ones that prevent it (e.g. HDL), as well as all tissue and serum GGT isoforms, could bring about substantial advances in the prevention of cardiovascular diseases, the development of cardiovascular and metabolic drugs, as well as the diagnosis and differential diagnosis of pathologies in which increasing GGT levels or the modification of its isoforms may play an important role.

However, such studies cannot be carried out with the currently available techniques of GGT assaying, in that all procedures that involve proteolysis (isoelectrofocusing, anionic exchange and affinity chromatography, etc.) result in GGT detachment from the different plasma carriers.

The differential migration of proteins in electrophoresis-based procedures is due to a combination of several factors (such as charge, mass, volume, etc.), so it is not possible to determine the precise nature of each band by these techniques, since the formation of each single band is determined by the concurrent action of several factors.

Procedures could be used in which lipoproteins are separated by precipitation with polycations (for example by precipitating a single lipoprotein class and assaying for the amount of GGT precipitated therewith), but these techniques do not offer sufficient specificity, as the precipitation of the different lipoproteins is not sufficiently selective and is excessively affected by temperature and pH conditions.

Lipoprotein separation could be accomplished by density gradient ultra-centrifugation techniques, in which the different lipoprotein classes are separated by virtue of their different density by centrifuging serum or plasma samples in continuous or stepwise gradients. However, such procedures involve using apparatuses (ultracentrifuges) that are not very common in biologic analysis laboratories and especially require very long centrifuging times (in the order of tens of hours) which may cause deterioration of the samples.

Thus, there is a need for a method for detecting serum GGT isoforms which is sensitive enough to allow for detection of the enzyme even in the range of values that are considered non-pathological (sGGT 5-50 U/L).

Such an assay would make it possible to discriminate and quantify the different serum GGT isoforms, or the different patterns of serum GGT isoforms, allowing the correlation between each isoform or isoform pattern and specific pathologies to be studied. This would bring about an improved diagnostic ability as well as remarkable savings in both human and economic cost terms.

Therefore, one object of the present invention is to provide a method of detecting serum gamma-glutamyl transferase (sGGT) isoforms in a sample of biological fluid, which is more sensitive, accurate, simple and cost-effective than the methods disclosed in the prior art.

Another object of the present invention is to provide a method of detecting sGGT isoforms in a sample of biological fluid, which allows for the identification and quantification of the various sGGT isoforms in the sample.

A further object of the present invention is to provide a method of detecting sGGT isoforms in a sample of biological fluid, which allows for the identification of the isoforms based on a single chemo-physical parameter, i.e. molecular weight, in order to allow for the quantification of the GGT physically associated with each lipoprotein class.

These and other objects are achieved by a method of detecting serum gamma-glutamyl transferase (sGGT) isoforms in a sample of biological fluid, comprising the following steps:
(a) separation of the serum proteins existing in the sample by high performance liquid chromatography (HPLC) with the aid of a gel filtration HPLC column suitable for the separation of serum proteins based on molecular weight, so as to achieve the separation of the serum proteins into different fractions and the consequent separation of the different sGGT isoforms complexed to each fraction respectively;
(b) post-column reaction of each protein fraction obtained in the previous step with a gamma-glutamyl transferase (GTT) substrate capable of forming a product detectable in the presence of GGT in such a protein fraction;
(c) determining the presence or absence of a detectable product in each protein fraction, the presence of a detectable product in a given protein fraction indicating the presence of the complexed GGT isoform in the said protein fraction.

The detection of the sGGT isoforms according to the method of the invention can be performed on any sample of biological fluid containing GGT, such as for example plasma, serum, urine, and also cell culture and bacterial culture supernatant.

The following detailed description, given by way of a non-limiting example, refers to the attached figures, wherein.

Figure 1:
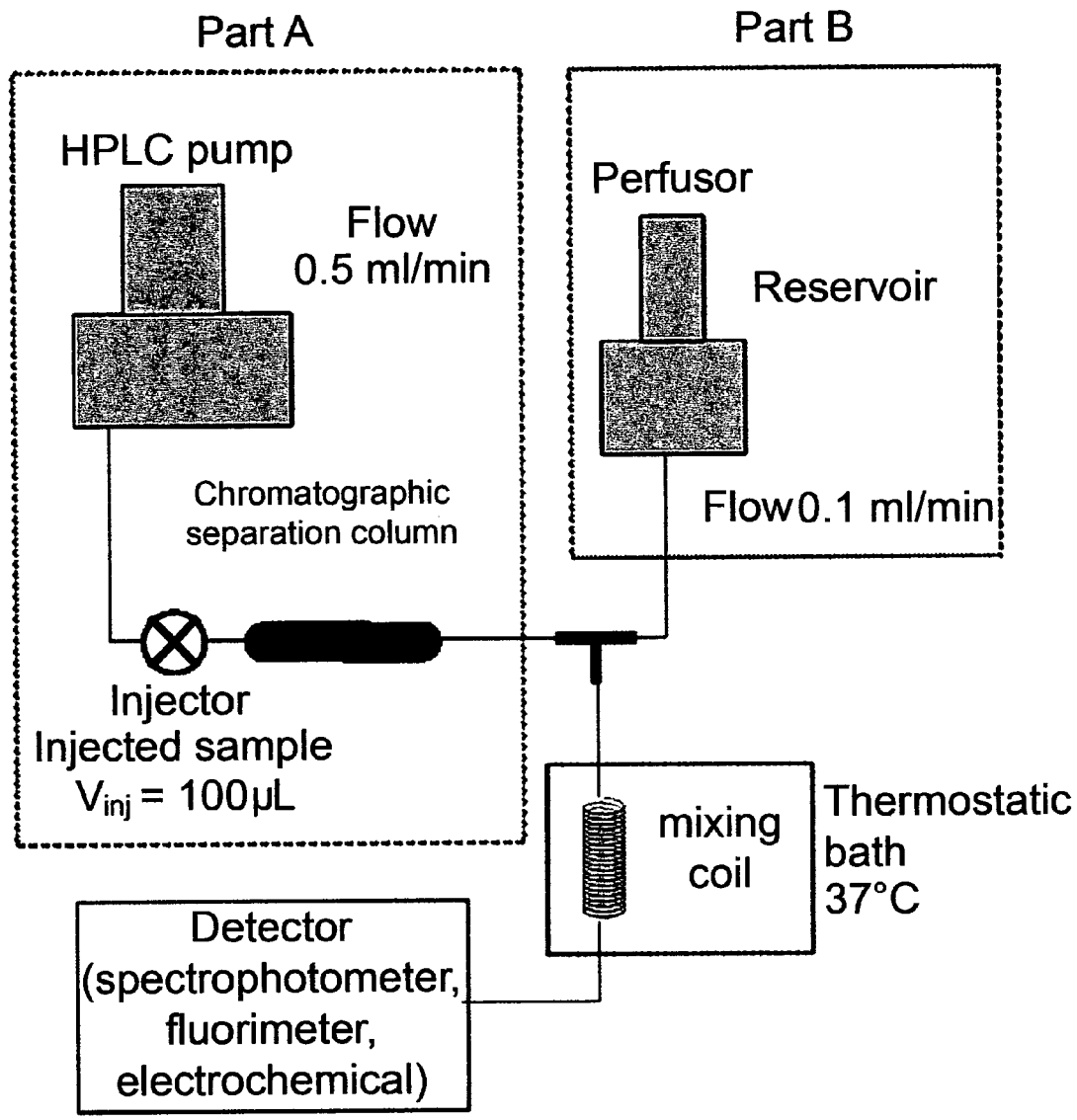
FIG. 1 is a schematic representation of the method of the invention and the equipment that may be used to carry out the same.

Referring to FIG. 1, the method of the invention can be performed by using a high performance liquid chromatography (HPLC) device, which exhibits the advantage of substantially being in every analysis laboratory. Furthermore, the method contemplates an on-line post-column reaction of the GGT enzyme with a GGT substrate designed to generate a detectable product, preferably a coloured (chromophore) or fluorescent compound (detectable by spectrophotometer and fluorimeter, respectively). The liquid chromatographer is advantageously a broadly-used, automatizable, controlled-cost instrument which is suitable for routine analysis, that can also be used by unskilled workers. The liquid chromatographer allows for separation of the single components constituting a mixture.

Part A of FIG. 1 represents the chromatographic separation of the biological fluid sample to be analysed with the aid of a high performance liquid chromatographer (HPLC) fitted with a pump, an injection valve and a separation column. The injected sample is passed through the separation column, i.e. an HPLC column designed to separate the GGT isoforms according to their molecular weight, so as to achieve elution of different protein fractions from the column, which are characterised by a specific molecular weight.

Part B of FIG. 1 represents the mixing of the column-eluted fractions with a GGT substrate designated to generate a detectable product, particularly a coloured (for example γ-glutamyl-4-nitroanilide) or fluorescent (for example γ-glutamyl-7-amido-4-methylcoumarin) compound, in the presence of a suitable concentration of an acceptor for the GGT-catalysed transpeptidization reaction. The mixing of the various column-eluted fractions with the GGT substrate occurs in a mixing coil placed into a thermostatic bath at a temperature suitable to accelerate the on-line post-column enzymatic reaction, for instance a temperature of 37° C. The solution containing the substrate for the on-line post-column enzymatic reaction is delivered from a syringe pump (for example a common perfusor for clinical use fitted with a tank or reservoir). Finally, the coloured or fluorescent product is detected by recording the absorbance or fluorescence of the flux exiting the mixing coil (effluent).

The activity (amount) of GGT present in each eluted fraction and the molecular size of the relative enzymatic isoform are determined according to the peak area (quantity) and retention time in the column (molecular weight).

The following examples are given for illustrative purposes only and are not to be construed as limitation of the scope of the invention as specified in the attached claims.

Principles

Isoform Separation

Chromatography techniques and, in particular, high performance liquid chromatography (HPLC) allow two or more components of a mixture to be separated by exploiting the affinity balance between a stationary phase placed within a chromatography column and a mobile phase flowing through the same column. The principle underlying this technique is that a substance with higher affinity for the stationary phase than the mobile phase takes longer to run through the chromatography column compared to a substance with low affinity for the stationary phase and high affinity for the mobile phase. The sample to be tested is injected on top of the chromatography column and, in the HPLC technique, is driven through the stationary phase by the mobile phase by means of application of a high pressure. In order to achieve an extremely efficient separation, which is a feature of HPLC, the size of the loading particles needs to be very small. The application of a high pressure is essential to keep a suitable eluent rate flow, and hence an adequate analysis time. A detector, for example a fluorimeter, a spectrophotometer, or an electro-chemical device, and a computer for identifying and/or quantifying the substances in the fractions as they elute from the column, are located at the bottom of the column.

HPLC chromatography allows for the identification and quantification of the various plasma GGT isoforms. In this specific case, the GGT isoforms, as they have significantly different molecular sizes, are retained in the column with different affinity and hence they exhibit different retention volumes ($v_R$).

The use of a gel filtration column enables the separation of molecules of different size by virtue of the fact that the stationary phase microporous material contains clefts (pores) of different size, so that the bigger molecules have proportionally less room to move in the stationary phase. Thereby, the injection of a buffer solution into the column at a constant rate makes the bigger molecules move at a proportionally higher speed, these molecules having a more limited volume for movement. Rather, the smaller molecules, being able to enter both the bigger pores and the smaller ones, into which the bigger molecules do not gain access, move more slowly through the column. By using gel filtration columns, and conveniently choosing the porosity of the material, it is possible to separate the plasma lipoproteins, as is described for example by Usui et al. (25) and Okazaki et al. (26).

Finally, injecting a reagent capable of generating a detectable reaction in the presence of GGT at a constant rate downstream of the column allows for the assessment of the amount of GGT in each lipoprotein fraction, each fraction being characterized by a different molecular weight and therefore by a different retention time in the column.

Detection of the Isoforms

The overall GGT-catalysed reaction can be concisely represented as follows:

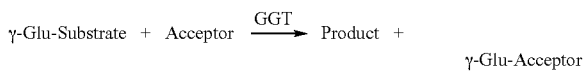

γ-Glu-Substrate + Acceptor $\xrightarrow{GGT}$ Product + γ-Glu-Acceptor

This reaction is known to proceed by the following modified ping-pong mechanism (27, 28):

Step (1): the enzyme binds the gamma-glutamyl group-donor substrate and releases the first reaction product:

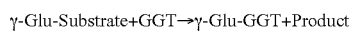

$$\gamma\text{-Glu-Substrate} + \text{GGT} \rightarrow \gamma\text{-Glu-GGT} + \text{Product}$$

Step (2): the resulting gamma-glutamyl acyl-enzyme (γ-Glu-GGT) can react with water (hydrolysis) or with an acceptor substrate (typically an amino acid or a dipeptide, such as for instance glycylglycine) giving, in the second reaction step (deacylation), glutamate or a transpeptide product, respectively:

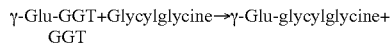

$$\gamma\text{-Glu-GGT} + \text{Glycylglycine} \rightarrow \gamma\text{-Glu-glycylglycine} + \text{GGT}$$

A further innovatory aspect of the present invention, besides separating the isoforms according to a single chemo-physical parameter, consists in carrying out a sensitive and selective detection system for GGT isoforms based on an on-line post-column enzymatic reaction, wherein the above described reaction between GGT and substrate is performed in a mixing coil downstream of the chromatographic separation.

For the detection of GGT activity, it is necessary to use a gamma-glutamyl group-donor substrate designated to generate a reaction product having different chemo-physical features and therefore detectable by a suitable detection device. Synthetic substrates for detecting GGT (such as γ-glutamyl-7-amido-4-methylcoumarin, γ-glutamyl-4-methoxy-naphtylamide, γ-glutamyl-4-nitroanilide, gamma-glutamyl-3-carboxy-4-nitroanilide, γ-glutamyl-3,5-dibromo-4-hydroxyanilide) fulfil such requirements.

In the specific embodiment example of the invention given herein below, the substrate γ-glutamyl-7-amido-4-methylcoumarin (γ-Glu-AMC) was used, which is a fluorescent molecule that, after reaction of the GGT, gives the product 7-amino-4-methylcoumarin (AMC), according to the following transpeptidization reaction:

$$\gamma\text{-Glu-AMC} + \text{Glycylglycine} \xrightarrow{\text{GGT}} \gamma\text{-Glu-glycylglycine} + \text{AMC}$$

The product AMC exhibits a different fluorescence excitation/emission spectrum from that of the starting substrate, γ-Glu-AMC (29), and can be detected by using a fluorimeter operating at an excitation wavelength of 380 nm ($\lambda_{ex}=380$ nm) and at an emission wavelength of 440 nm ($\lambda_{em}=440$ nm). The fluorimetric detection presents the advantage of being sensitive, showing a detection limit for the GGT enzyme of 0.1 mU.

However, the activity of GGT complexed to the different protein fractions eluted from the chromatography column can be determined by using other commercially available detection devices (UV-visible spectrophotometer, electrochemical detector), according to the type of substrate chosen.

In the specific embodiment example here described, the mixture containing the donor substrate γ-Glu-AMC deriving from the perfusor (FIG. 1, part B) is mixed under continuous flow with the eluate deriving from the chromatography column (FIG. 1, part A). The donor substrate reacts with the eluate coming out from the chromatography column. Since the fluorescent product AMC specifically forms only in the presence of the GGT enzyme, the fluorescence signal is seen only with the elution of the GGT isoforms.

This procedure allows the retention volume ($V_R$), and hence the molecular weight, of plasma GGT isoforms to be visualised.

The reaction mix used for the enzymatic on-line post-column reaction according to this embodiment preferably contains the following components in the following quantities:

0.25 M TRIS buffer, pH 8.3;
180 μM γ-Glu-AMC;

The chromatographic eluent phase present in the reservoir of the HPLC pump preferably contains the following components in the following quantities:

0.1 M phosphate buffer, pH 7.4 containing 0.2 M NaCl and 0.1 mM EDTA;
5.4 mM Glycyl-glycine (GG, acceptor of gamma-glutamyl groups).

The optimal operation conditions for detecting the GGT isoforms by liquid chromatography coupled with on-line post-column derivitization with the substrate γ-Glu-AMC and spectrofluorometric detection ($\lambda_{ex}=380$ nm and $\lambda_{em}=440$ nm) are shown in Table I below:

TABLE I

| | |
|---|---|
| HPLC flow | 0.5 mL/min |
| derivitization mix flow | 0.1 mL/min |
| Volume of sample injected ($V_{inj}$) | 100 μL |
| gGluAMC final concentration | 30 μM |
| Volume of the mixing coil | 2.6 mL |
| Temperature of the thermostatic bath | 37° C. |

Figure 2:
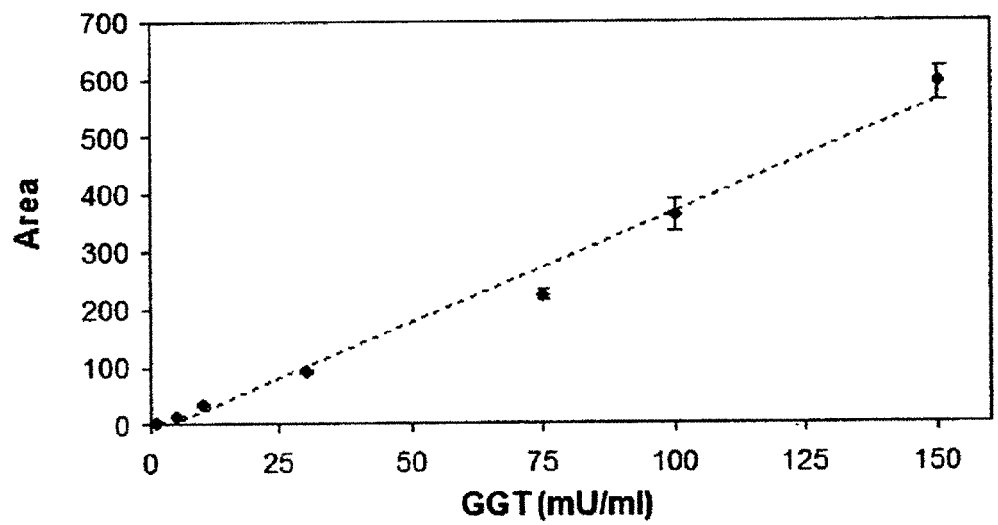
FIG. 2 shows the GGT standard calibration curve obtained by injecting GGT into the HPLC column at different concentrations.

FIG. 2 shows the calibration curve of the GGT standard (commercial preparation of bovine kidney GGT dissolved in 0.1 M phosphate buffer pH 7.4) obtained by injecting different concentrations of GGT. The calibration showed in FIG. 2 was carried out under the operation conditions reported in Table I with the FIA (Flow Injection Analysis) technique, that is with the system in FIG. 1 but in the absence of a chromatography column. Such a technique allows analogous responses (peak area) to those obtained in the presence of the separation column to be obtained, but in less time (approximately 4 minutes versus approximately 50 minutes) and can be used advantageously with a commercial standard for the calibration of the system. The experimental points obtained are linear in the range of three magnitude orders, with a dynamic linear range of 0.5-150 mU/ml (corresponding to a range of 0.05-15 mU), with a sensitivity factor of 3.806±0.116 area·ml/mU ($R^2=0.952$, N=8 points), and a detection limit of 0.5 mU/ml ($LOD_C=0.167$ mU/ml). The standard deviation refers to N=7 replicas of the same experimental point.

EXPERIMENTAL EXAMPLE

Detecting the GGT Isoforms in Human Plasma (1) Preparation of a Plasma Standard Sample A plasma standard sample was obtained by mixing plasma obtained from 10 subjects in equal parts. The pool thus obtained was divided into 150 μl aliquots, which were stored at −20° C. until use.

(2) HPLC

A chromatography column with the following characteristics was used: Superose-6 10/300 GL molecular filtration column (GE Healthcare) with a particle diameter of 13 μM, 30 cm length, 1 cm diameter. 0.1 M phosphate buffer, pH 7.4, containing 0.2 M NaCl, 0.1 mM EDTA, and 5.4 mM glycylglycine, was used as the eluent. A 100 μL (injection volume) injection loop was used. Isocratic elution conditions with a 0.5 mL/min flow were used.

(3) Mixture for the Post-Column Derivitization Reaction

The substrate stock solution, 3.6 mM γ-Glu-AMC, was prepared in 0.005 N NaOH and stored at +4° C. The mixture for the post-column derivitization reaction, 180 μM γ-Glu-AMC, was prepared daily in 0.25 M TRIS buffer, pH 8.3.

(4) Preparation of the Sample

The periphery whole blood (3 mL) from the subject to be analysed was sampled in a Vacutest tube in the presence of EDTA as an anticoagulant. The blood was centrifuged at 1500×g for 10 minutes at 4° C. in order to remove the particulate matter and obtain the plasma. The plasma thus obtained was injected into the system of FIG. 1 diluted 1:2 with the eluent phase.

(5) Analysis Procedure

The system was calibrated by the daily injection of the standard plasma diluted 1:2 with the eluent phase. The diluted plasma sample was injected into the loop of the system described in FIG. 1.

Figure 3:
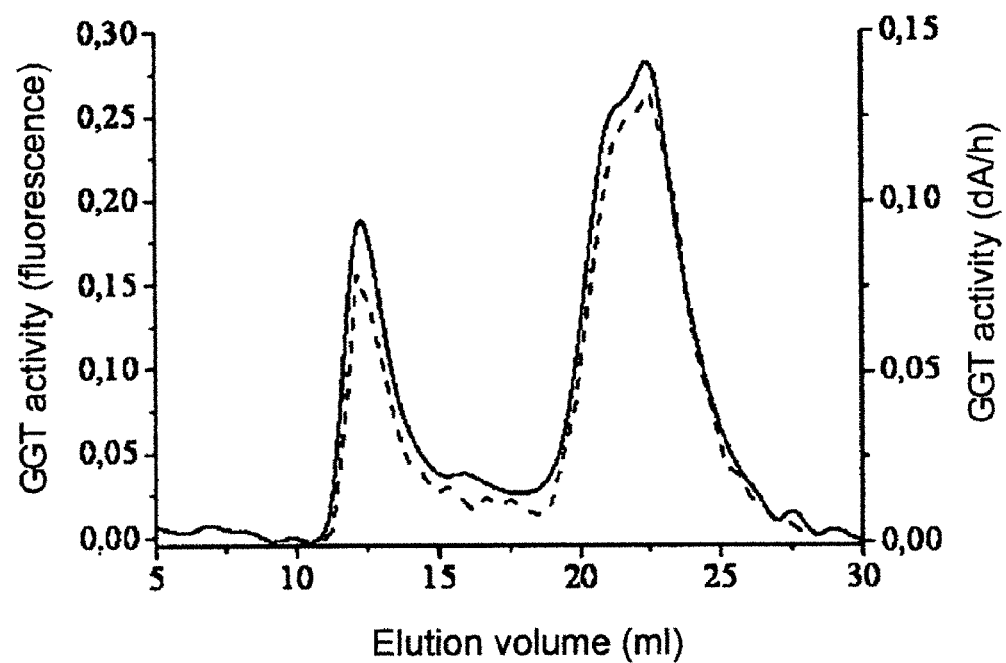
FIG. 3 shows two chromatograms obtained from a plasma sample injected into the system of FIG. 1. Solid line: on-line fluorescence chromatogram achieved by using γ-Glu-AMC as a substrate for the reaction of GTT ($\lambda_{ex}$=380 nm and $\lambda_{em}$=440 nm); broken line: at-line chromatogram at λ=405 nm achieved by using γ-Glu-4-NA as a substrate.

FIG. 3 superimposes the typical chromatographic plots achieved by using the fluorescent substrate γ-Glu-AMC and the chromophore substrate γ-glutamyl-4-nitroanilide (γ-Glu-4-NA). In both cases, the chromatography was carried out under the following conditions: Superose-6 10/300 GL column (GE Healthcare); injection loop=100 μL; 0.5 ml/min isocratic elution in 0.1 M phosphate buffer pH 7.4, containing 0.2 M NaCl, 0.1 mM EDTA, and 5.4 mM glycylglycine as the acceptor. Derivitizating flow of the fluorescent substrate=0.1 mL/min.

In the former case, the GGT elution profile was detected by using the system of FIG. 1 and the fluorescent substrate γ-Glu-AMC. In the latter case, the eluate from the chromatography column of the system in FIG. 1 was collected in 0.5 ml fractions and the activity of each one of them was detected with the enzymatic kinetic assay (30) based on the breakdown of the chromophore substrate γ-Glu-4-NA with the release of a coloured product (λ=405 nm) that is proportional to the GGT activity in the fraction.

Figure 4:
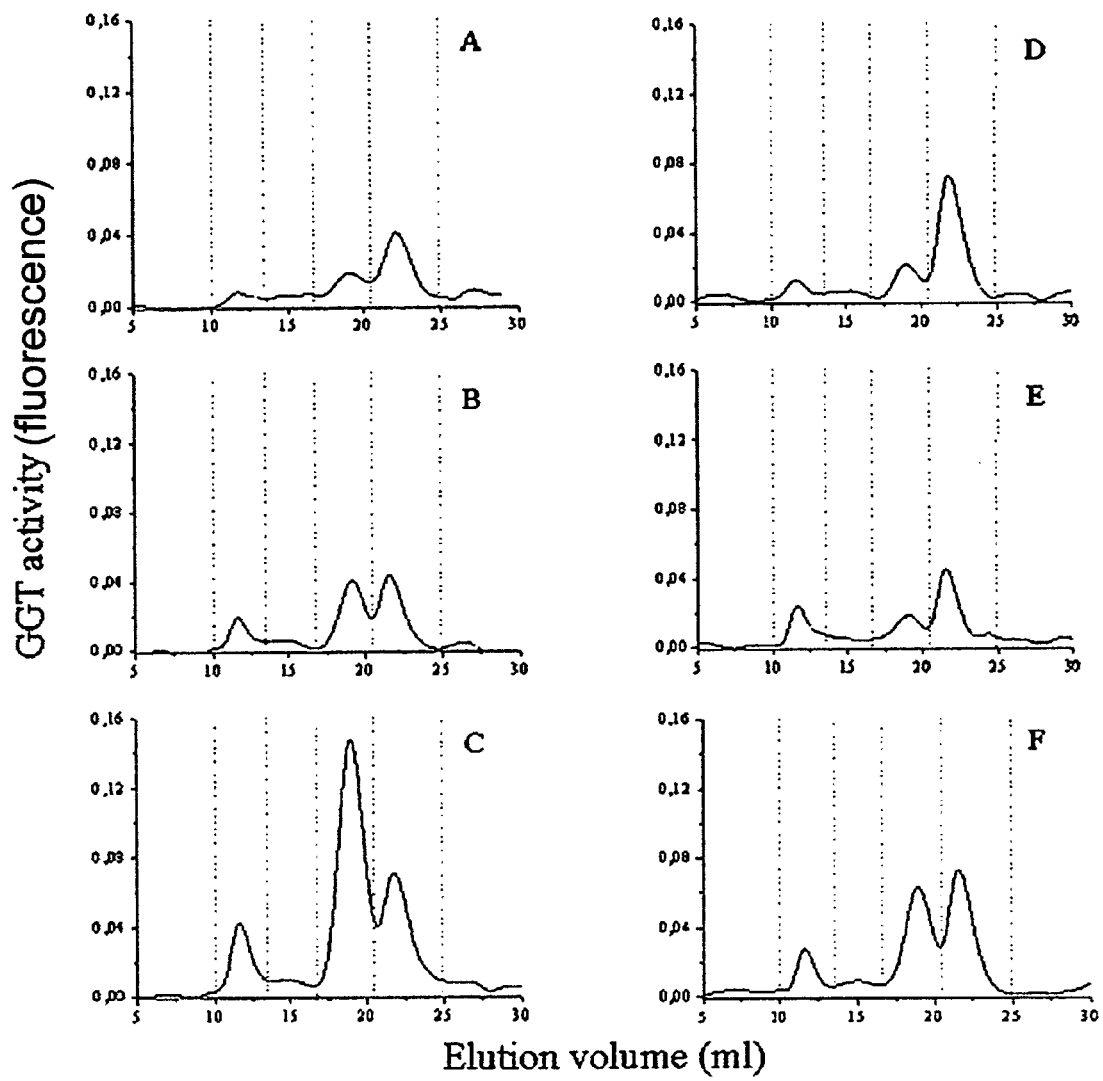
FIG. 4 shows GGT activity distribution profiles achieved by injecting plasma samples obtained from control subjects (blood donors) into the system of FIG. 1, under the conditions reported in Table I.

In FIG. 4, the chromatographic plots obtained by injecting plasma samples from different control subjects and using γ-Glu-AMC as the substrate for the detection of GGT activity are shown by way of example. Four activity peaks can be seen, corresponding to the different GGT isoforms at $V_R$=11.6; 14.8; 18.9; 21.7 ml, corresponding to fractions characterised by molecular weights of approximately 2000, 940, 140, and 70 Kda, respectively.

The GGT concentration associated with each peak is determined on the basis of the peak area and the calibration curve. Alternatively, the ratio between the area under the whole chromatogram and the total enzymatic activity of GGT measured on the plasma sample (taking account of the dilution factor) can be taken as the reference.

As the molecular weights associated with each of the GGT activity peaks correspond to those of the lipoprotein classes in the plasma, plasma samples were ultra-centrifuged in density gradients in order to separate the major lipoprotein classes (VLDL, LDL, HDL). The lipoprotein fractions so obtained were then injected into the system schematised in FIG. 1 in order to evaluate the GGT content.

Figure 5:
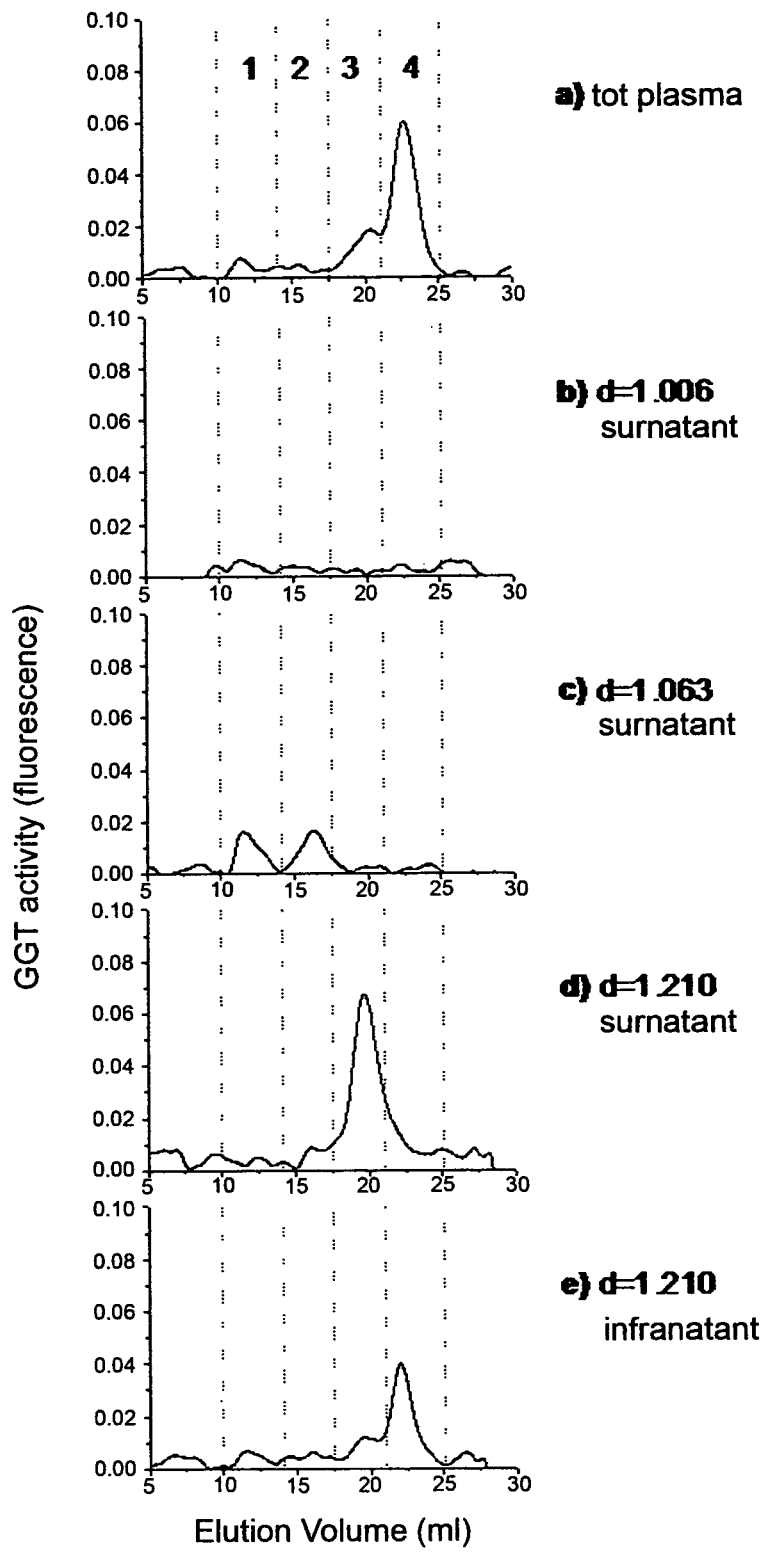
FIG. 5 shows GGT activity in plasma and in the respective lipoprotein fractions obtained by ultra-centrifugation at different densities.

As can be seen in FIG. 5, while the total plasma plot (a) shows activity fractions in the regions indicated by the numbers 1-4, the injection of purified VLDLs alone (b) shows no peak, whereas the plasma enriched in LDL (c) and HDL (d) shows increased peaks in the regions 1 and 2 (c) and 3 (d), respectively. Finally, the plasma depleted of lipoproteins shows a reduction in all the bands, except for the band 4.

Therefore, the ultra-centrifugation of the plasma in different densities allowed three sGGT isoforms to be separated: the forms 1 and 2 (molecular weights of 2000 and 940 KDa, respectively) float at d=1.063; the form 3 of molecular weight of 140 KDa floats at d=1.21. Such densities correspond to LDLs and HDLs, respectively, which thus confirms that the circulating GGT associates with these lipoprotein fractions. On the other hand, the sGGT form 4 (70 KDa) is not found in any of the lipoprotein fractions, and could therefore correspond to the plasma-soluble enzyme, as is also suggested by the molecular weight.

Bibliographic References

1. Wannamethee G, Ebrahim S, Shaper A G. Gamma-glutamyltransferase: determinants and association with mortality from ischaemic heart disease and all causes. Am J Epidemiol. 1995; 142: 699-708.
2. Ruttmann E., Brant L. J., Concin H., Diem G, Rapp K., Ulmer H. γ-Glutamyltransferase as a risk factor for cardiovascular disease mortality. An investigation in a cohort of 163,944 Austrian adults. Circulation. 2005; 112: 2130-7.
3. Lee D S, Evans J C, Robins S J, Wilson P W, Albano I, Fox C S, Wang T J, Benjamin E J, D'Agostino R B, Vasan R S. Gamma glutamyl transferase and metabolic syndrome, cardiovascular disease, and mortality risk: the Framingham Heart Study. Arterioscler Thromb Vasc Biol. 2007; 27: 127-33.
4. Kazemi-Shirazi L, Endler G, Winkler S, Schickbauer T, Wagner O, Marsik C. Gamma Glutamyltranspeptidase and Long-Term Survival: Is It Just the Liver? Clin Chem 2007; 53: 940-946.
5. Huseby N E, Ingebretsen O C. The level of gamma-glutamyltransferase in serum, effect of carbohydrate heterogeneity on clearance rate. Scand J Clin Lab Invest Suppl. 1993; 215: 93-100.
6. Hanigan M H, Frierson H F Jr, Immunohistochemical detection of gamma-glutamyl transpeptidase in normal human tissue. J Histochem Cytochem. 1996; 44: 1101-8.
7. Hanigan M H, Frierson H F Jr, Swanson P E, De Young B R. Altered expression of gamma-glutamyl transpeptidase in human tumors. Hum Pathol 1996; 30: 300-5.
8. Khalaf M R, Hayhoe F G. Cytochemistry of γ-glutamyltransferase in haemic cells and malignancies. Histochem J. 1987; 19: 385-95.
9. Meister A. Glutathione metabolism. Methods Enzymol. 1995; 251: 3-7.
10. Dominici S, Paolicchi A, Lorenzini E, Maellaro E, Comporti M, Pieri L, Minotti G, Pornpella A. Gamma-glutamyltransferase-dependent prooxidant reactions: a factor in multiple processes. Biofactors. 2003; 17: 187-98.
11. Pompella A, De Tata V, Paolicchi A, Zunino F. Expression of gamma-glutamyltransferase in cancer cells and its significance in drug resistance. Biochem Pharmacol. 2006; 71: 231-8.
12. Nemesanszky E, Lott J A. Gamma-glutamyltransferase and its isoenzymes: progress and problems. Clin Chem. 1985; 31: 797-803.
13. Courtay C, Heisterkamp N, Siest G, Groffen J. Expression of multiple γ-glutamyltransferase genes in man. Biochem J. 1994; 297: 503-8.
14. Evjen G, Huseby N E. Characterization of the carbohydrate moiety of human gamma-glutamyltransferases using lectin-blotting and glycosidase treatment. Clin Chim Acta. 1992; 209:27-34.

15. Huseby N E. Separation and characterization of human gamma-glutamyltransferases. Clin Chim Acta. 1981; 111: 39-45.
16. Huseby N E. Multiple forms of serum gamma-glutamyltransferase. Association of the enzyme with lipoproteins. Clin Chim Acta. 1982; 124: 103-12.
17. Szasz G. A kinetic photometric method for serum gamma-glutamyl transpeptidase. Clin Chem. 1969; 15:124-36.
18. Kok P J M J, Seidel B, Holtkamp H C, Huisman J. A new procedure for the visualization of multiple forms of gamma-glutamyltransferase (GGT). Clin Chim Acta. 1978; 90, 209-216.
19. Castaldo G, Intrieri M, Castellano L, de Sio I, Del Vecchio Blanco C, Sacchetti L, Salvatore F. Serum gamma-glutamyltransferase isoform complexed to LDL in the diagnosis of small hepatocellular carcinoma. Clin Chem. 1999; 45:1100-2.
20. Pompili M, Addolorato G, Pignataro G, Rossi C, Zuppi C, Covino M, Grieco A, Gasbarrini G, Rapaccini G L. Evaluation of the albumin-gamma-glutamyltransferase isoenzyme as a diagnostic marker of hepatocellular carcinoma-complicating liver cirrhosis. J Gastroenterol Hepatol. 2003; 18:288-95.
21. Emdin M, Passino C, Michelassi C, Titta F, L'Abbate A, Donato L, Pompella A, Paolicchi A. Prognostic value of serum gamma-glutamyl transferase activity after myocardial infarction. Eur Heart J. 2001; 22: 1802-7.
22. Emdin M, Passino C, Donato L, Paolicchi A, Pompella A. Serum gamma-glutamyltransferase as a risk factor of ischemic stroke might be independent of alcohol consumption. Stroke. 2002; 33: 1163-4.
23. Paolicchi A, Emdin M, Ghliozeni E, Ciancia E, Passino C, Popoff G, Pompella A. Human atherosclerotic plaques contain gamma-glutamyl transpeptidase enzyme activity. Circulation. 2004; 109: 1440.
24. Paolicchi A, Minotti G, Tonarelli P, Tongiani R, De Cesare D, Mezzetti A, Dominici S, Comporti M, Pompella A. Gamma-glutamyl transpeptidase-dependent iron reduction and LDL oxidation—a potential mechanism in atherosclerosis. J Investig Med. 1999; 47: 151-60.
25. Usui S, Hara Y, Hosaki S, Okazaki M. A new on-line dual enzymatic method for simultaneous quantification of cholesterol and triglycerides in lipoproteins by HPLC. J Lipid Res. 2002; 43:805-14.
26. Okazaki M, Usui S, Ishigami M, Sakai N, Nakamura T, Matsuzawa Y, Yamashita S. Identification of unique lipoprotein subclasses for visceral obesity by component analysis of cholesterol profile in high-performance liquid chromatography. Arterioscler Thromb Vasc Biol. 2005; 25:578-84.
27. Allison R D. γ-Glutamyl transpeptidase: kinetics and mechanism. Methods Enzymol. 1985; 113:419-437.
28. Taniguchi N, Ikeda Y. γ-Glutamyl transpeptidase: catalytic mechanism and gene expression. Adv Enzymol Relat Areas Mol. Biol. 1998; 72:239-278.
29. Smith G D, Ding J L, Peters T J. A sensitive fluorimetric assay for γ-Glutamyl transferase. Analytical Biochemistry. 1979; 100: 136-139.
30. Huseby N E, Stromme J H. Practical points regarding routine determination of γ-glutamyltransferase (γ-GT) in serum with a kinetic method at 37° C. Scand J Clin Lab Invest. 1974; 34: 357-63.

The invention claimed is:

1. A method of detecting serum gamma-glutamyl transferase isoforms in a biological fluid, comprising the following steps:
providing a sample of said biological fluid;
providing a High Performance Liquid Chromatography (HPLC) column, said HPLC column designed to separate protein fractions according to their molecular weight;
injecting the sample through the HPLC column to separate the proteins in the sample;
obtaining from the HPLC column an eluate in which protein fractions are separated from each other by their specific molecular weight; wherein said protein fractions are separated from each other in such a way that any different gamma-glutamyl transferase isoforms can be associated with each protein fraction respectively;
causing said protein fractions of said eluate to react in turn with a gamma-glutamyl transferase substrate from which a product can be formed that is detectable only if a respective GGT isoform in each protein fraction is present;
determining in each protein fraction the presence or absence of any of said detectable product responsive to the presence or absence in each protein fraction of said respective detectable product;
wherein at least one of four different gamma-glutamyl transferase isoforms is sought in said protein fractions, which correspond to respective molecular weights selected among approximately 2000, 940, 140, and 70 kDa.

2. The method according to claim 1, wherein the separation step is carried out with a gel filtration HPLC column.

3. The method according to claim 1, wherein the detectable product that forms in the presence of gamma-glutamyl transferase is a chromophore or a fluorescent compound.

4. A method according to claim 1, wherein the reaction causing said protein fractions to react in turn with a gamma-glutamyl transferase substrate is carried out in the presence of an acceptor of gamma-glutamyl groups.

5. The method according to claim 4, wherein the acceptor of gamma-glutamyl groups is glycylglycine.

6. The method according to claim 1, wherein the gamma-glutamyl transferase substrate that forms a product detectable in the presence of gamma-glutamyl transferase is selected from the group consisting of gamma-glutamyl-7-amido-4-methylcoumarin, gamma-glutamyl-4-methoxy-naphtylamide, gamma-glutamyl-4-nitroanilide, gamma-glutamyl-3-carboxy-4-nitroanilide, and gamma-glutamyl-3,5-dibromo-4-hydroxy-anilide.

7. The method according to claim 6, wherein the gamma-glutamyl transferase substrate that forms a product detectable in the presence of gamma-glutamyl transferase is gamma-glutamyl-7-amido-4-methylcoumarin and the detectable product is 7-amino-4-methylcoumarin.

8. A method according to claim 1, comprising the determination of the presence of gamma-glutamyl transferase in each protein fraction and the quantification of gamma-glutamyl transferase activity.

9. The method according to claim 8, comprising the steps of: (a) separation of the proteins existing in the sample by high performance liquid chromatography (HPLC) with the aid of an HPLC column suitable for the separation of serum proteins based on molecular weight (or molecular size), as to achieve separation of serum proteins into different fractions and consequent separation of the different gamma-glutamyl transferase isoforms associated with each fraction respectively; (b) post-column reaction of each protein fraction obtained in the previous step with the substrate gamma-glutamyl-7-amido-4-methylcoumarin that forms the fluorescent product 7-amido-4-methylcoumarin in the presence of gamma-glutamyl transferase in such a protein fraction; (c)

determination and quantification of the product 7-amido-4-methylcoumarin in each protein fraction by fluorimetry, using an excitation wavelength of 380 nm and an emission wavelength of 440 nm.

10. A method according to claim 1, wherein the biological fluid is selected from the group consisting of plasma, serum, urine, cell culture and bacterial culture supernatant.

11. A method according to claim 1, further comprising separating the gamma-glutamyl transferase isoforms.

* * * * *